United States Patent [19]

Lang et al.

[11] Patent Number: 5,192,332

[45] Date of Patent: Mar. 9, 1993

[54] COSMETIC TEMPORARY COLORING COMPOSITIONS CONTAINING PROTEIN DERIVATIVES

[75] Inventors: Gérard Lang, Saint-Gratien; Serge Forestier, Claye-Souilly; Gérard Malle, Villiers-Sur-Morin; Alex Junino, Aulnay-Sous-Bois, all of France

[73] Assignee: L'Oreal, Paris, France

[21] Appl. No.: 771,478

[22] Filed: Oct. 7, 1991

Related U.S. Application Data

[63] Continuation-in-part of Ser. No. 447,532, Dec. 7, 1989, abandoned.

[30] Foreign Application Priority Data

Oct. 14, 1983 [LU] Luxembourg .......................... 85 047

[51] Int. Cl.$^5$ .............................................. A61K 7/13
[52] U.S. Cl. ............................................ 8/405; 8/406; 8/408; 8/423; 424/70
[58] Field of Search ................... 8/405, 406, 408, 423; 424/70

[56] References Cited

U.S. PATENT DOCUMENTS 4,314,808  2/1982  Jacquet et al. ........................ 8/405
4,363,797  12/1982  Jacquet et al. ........................ 8/406

FOREIGN PATENT DOCUMENTS 1310583  10/1962  France .

Primary Examiner—A. Lionel Clingman
Assistant Examiner—William S. Parks
Attorney, Agent, or Firm—Cushman, Darby & Cushman

[57] ABSTRACT

The present invention provides a cosmetic temporary coloring composition which comprises a cosmetically acceptable support and, as an active ingredient, at least one chemically modified protein derivative which contains residues of molecules of dye grafted onto the protein chain. Thus, certain of the side chains of the protein derivative having amine, alcohol or thiol functions are substituted by residues of dye molecules. The present invention further provides a process for the temporary coloring of human hair, nails or skin comprising applying thereto in an amount effective to color the human hair, nails or skin a composition containing a solution in water, a lower mono-alcohol or polyol or an aqueous alcoholic mixture wherein the alcohol is present in an amount ranging from 0.5 to 50 percent by weight of the chemically modified protein derivative.

8 Claims, No Drawings

COSMETIC TEMPORARY COLORING COMPOSITIONS CONTAINING PROTEIN DERIVATIVES

This is a continuation-in-part of our application Ser. No. 07/447,532 filed Dec. 7, 1989, now abandoned.

BACKGROUND OF THE INVENTION

1. Field of the Invention

The present invention relates to cosmetic temporary coloring compositions which contain, as an active ingredient, at least one protein derivative which contains residues of molecules of dye grafted onto the protein chain. "Molecules of dye" as used herein refers to molecules which contain chromophoric or chromogenic groups. The coloring compositions of the invention may be used to color keratinous supports, such as keratin fibers, and, in particular, human hair, or may be applied to the surface of the skin.

2. Description of the Prior Art

Colored protein derivatives have been described in the literature, but they have never been proposed as active ingredients in cosmetic temporary coloring compositions. French Patent No. 1,310,583 describes substances obtained by grafting molecules of dye onto proteins, especially onto casein, these substances being used for permanently coloring viscose masses, as pigments or for dyeing synthetic resins.

Many protein hydrolyzates are known which have useful properties for treating the skin surface, or hair. It is known, furthermore, how to graft residues of molecules of dye onto chains of synthetic polymers. These grafted synthetic polymers can be used to produce coloring compositions; however, these polymers are generally only sparingly soluble in common cosmetic solvents, and they form films which are excessively rigid.

SUMMARY OF THE INVENTION

As noted above, the present invention relates to cosmetic temporary coloring compositions which contain, as an active ingredient, at least one protein derivative which contains residues of molecules of dye grafted onto the protein chain.

The present inventors have found that protein derivatives which incorporate residues of molecules of dye possess better properties than was expected. Due to the presence of the protein polymer chains and the coloring effect of the grafted molecules of dye, the following useful cosmetic properties are observed:

(1) the present protein derivatives are more soluble in common cosmetic solvents, particularly in water, than many colored synthetic polymers; and (2) after application to the skin, the colored proteins form, particularly in non-aqueous media, a flexible protective film which is better than that provided by known synthetic polymers.

(3) the coloration obtained is temporary and can be easily removed by washing.

As a result of these useful properties, the cosmetic coloring compositions of the present invention, in which the active ingredient consists of natural polymer chains onto which molecules of dye are grafted, is preferred to cosmetic coloring compositions which incorporate synthetic polymers having grafts of coloring materials.

DETAILED DESCRIPTION OF THE INVENTION

The present invention provides a cosmetic temporary coloring composition which comprises a cosmetically acceptable support and at least one chemically modified protein derivative of a protein, which protein derivative has a molecular weight of from 500 to 50,000, preferably from 5,000 to 30,000, of formula (I):

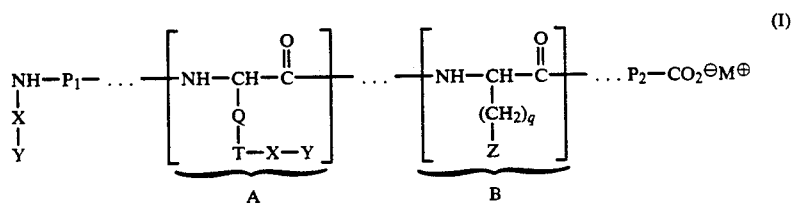

which is defined as follows.

Y is a residue of a molecule of dye (the term "residue" as used herein refers to the functional moiety of a molecule).

$P_1$ and $P_2$ are non-acylated chains of said protein which are not modified chemically by addition or nucleophilic substitution. Amino acids of proteins have the general formula, $$H_2N-CH(R')-COOH$$

wherein R' is the side chain (see L. Stryer, Biochemistry, 2nd Edition, W. H. Freeman and Co., San Francisco, 1981, the entire disclosure of which is hereby incorporated by reference and relied upon).

According to the present invention, $P_1$ is a chain of aminoacid derivative units, represented by the formula

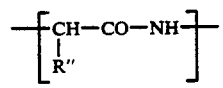

in which R" may be different from one unit to the other. For example, R" may be H (glycocoll derivative), $CH_3$ (alanine derivative), $CH_2\text{-}C_6H_5$ (phenylalanine derivative), $CH_2\text{-}CH_2\text{-}S\text{-}CH_3$ (methionine derivative). $P_2$ is a chain of aminoacid derivative units of formula

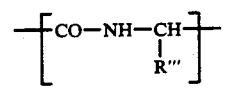

in which R'" can be different from one unit to the other and has the same meaning as R".

X is any group, or direct covalent bond, which joins the residue of a molecule of dye and the protein derivative.

M is hydrogen, alkali metal, magnesium, or $N^+(R_2)_4$, wherein each $R_2$, which may be the same or different, is hydrogen, alkyl having 1 to 4 carbon atoms or hydroxyalkyl having 1 to 4 carbon atoms.

T is O, NH or, when the amino acid of unit A contains cysteine, S.

Q is an alkyl, aryl or aralkyl group of the side chain of the amino acid which carries amino, alcohol or thiol group of unit A of the protein derivative. For example: Q is -$CH_2$ and T is O when the protein contains serine; Q is

and T is O when the protein contains threonine; Q is —$CH_2$— and T is S when the protein contains cysteine; Q is

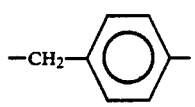

and T is O when the protein contains tyrosine; Q is -$(CH_2)_4$- and T is NH when the protein contains lysine; Q is

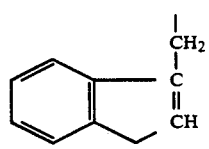

and T is NH when the protein contains tryptophane. q is an integer from 1 to 5 with the proviso that, when Z is $SO_3^-M^+$ or $SR_3$, q is 1 and the amino acid of unit B is cysteine.

Z is:

(1) $SO_3^-M^-$, wherein M has the meaning given above;

(2) $SR_3$, wherein $R_3$ is:

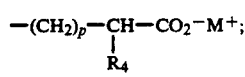  (II)

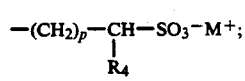  (III)

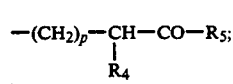  (IV)

wherein M has the meaning given above, p is 0 or an integer from 1 to 5, $R_4$ is a hydrogen atom or an alkyl group of 1 to 4 carbon atoms and $R_5$ is:

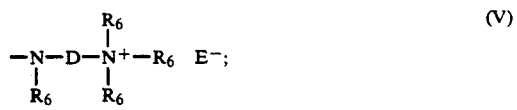  (V)

or

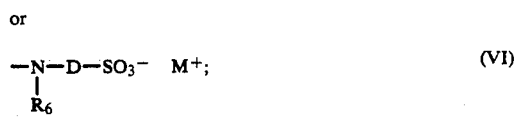  (VI)

wherein D is a linear or branched alkylene group of 2 to 10 carbon atoms, M has the meaning given above, the groups $R_6$, which may be the same or different, are hydrogen, alkyl having 1 to 4 carbon atoms or hydroxyalkyl having 1 to 4 carbon atoms, $E^-$ is a halide, $RCOO^-$, $RSO_3^-$ or $RSO_4^-$ ion, wherein R is a hydrocarbon group of 1 to 10 carbon atoms; or (3) an amino-terminal group from the amino acid of unit B of the protein derivative, which amino acid is basic and which amino-terminal group may be mono- or di-substituted with an $R_3$ group as defined above; with the proviso that Z is only $SO_3^-M^+$ or $SR_3$ when the amino acid of unit B contains cysteine. The basic amino acids are lysine, arginine and histidine, and the amino-terminal group is that which contains the amine function. Thus, when the basic amino acid is lysine, Z is —$NH_2$ and q is 4; when it is arginine, Z is

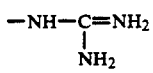

and q is 3; when it is histidine, Z is

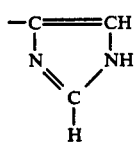

and q is 1. The NH or $NH_2$ functions present in Z can be alkylated by alkylating agents IIa, IIIa, IVa and $IV^1$a set forth below.

The units A make up 1 to 70% by weight of the protein derivative.

The units B make up 0 to 15% by weight of the protein derivative.

The protein from which the protein derivative of formula (I) is prepared may originate from many sources. Thus, the parent protein may be of animal origin and can originate from, for example, keratin, gelatin, egg albumin, blood serum albumin, casein or lactalbumin. The keratin can originate from, for example, hair, wool, horn, animal hairs, bristles or feathers. The parent protein may also be of vegetable origin, for example originating from soya, groundnut or cotton seed.

The protein derivative can be a protein hydrolyzate, which has been chemically modified for grafting the residues of molecules of dye after the hydrolysis from which it has arisen.

The group Y of the chemically modified protein derivative of formula (I) may be an azo dye residue, an anthraquinone dye residue, a naphthoquinone dye residue, a residue of a phthalocyanin derivative or a residue of a nitrated derivative of the benzene series.

More particularly, Y may be a residue of the azo dyes, anthraquinone dyes or phthalocyanin derivatives which are defined in "Color Index" (3rd Edition, Volume 3, pp. 3391 to 3560 [1971] and revised 3rd Edition, Volume 6, pp. 6265 to 6345 [1975]) under the designation "reactive", the residue -X- then being:

(1) 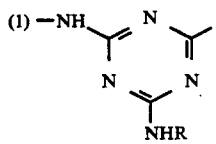

where R = 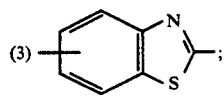 ;

(2) —SO₂—CH₂—CH₂—;

(3) 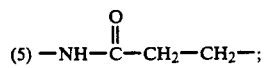;

(4) —SO₂—NH—CH₂—CH₂—;

(5) 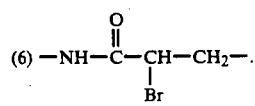;

or (6) 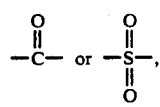.

Most particularly, Y may be a residue of the dyes defined in "Color Index" under the references:

| |
|---|
| CI 13 245 ("Reactive Yellow 3") |
| CI 14 824 ("Reactive Red 22") |
| CI 16 202 ("Reactive Red 23") |
| CI 17 865 ("Reactive Orange 2") |
| CI 17 756 ("Reactive Orange 7") |
| CI 17 757 ("Reactive Orange 16") |
| CI 17 910 ("Reactive Red 9") |
| CI 18 096 ("Reactive Violet 4") |
| CI 18 097 ("Reactive Violet 5") |
| CI 18 105 ("Reactive Red 4") |
| CI 18 156 ("Reactive Red 12") |
| CI 18 157 ("Reactive Violet 2") |
| CI 18 159 ("Reactive Red 3") |
| CI 18 852 ("Reactive Yellow 17") |
| CI 18 972 ("Reactive Yellow 2") |
| CI 18 990 ("Reactive Yellow 13") |
| CI 19 036 ("Reactive Yellow 14") |
| CI 61 200 ("Reactive Blue 19") |
| CI 61 210 ("Reactive Blue 5") |
| CI 61 211 ("Reactive Blue 2") |
| CI 74 460 ("Reactive Blue 7") |
| CI 74 459 ("Reactive Blue 15") |

Y may also originate from dyes possessing a carboxylic acid or sulphonic acid group, the residue -X- associated with these two Y residues being respectively

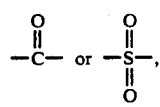

and the associated residue —T— being —NH.

Y may also be of the formulae:

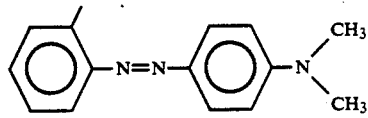

or

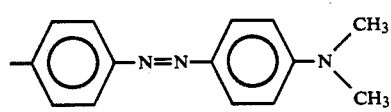

which may originate, respectively, from the following dyes:

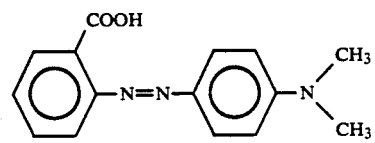

CI 13 020 ("CI Acid Red 2") and

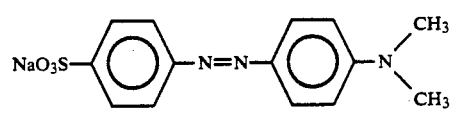

CI 13 025 ("CI Acid Orange 52").

If Y is either of these two groups, the grafting onto the protein chain is accomplished by the formation, respectively, of an amide or sulphonamide.

Y can also originate from dyes possessing a 2,3-epoxy-1-propyloxy function, in which case —X— is —CH₂—CHOH—CH₂—O— and —T— is —NH— or —O—.

Y may also be:

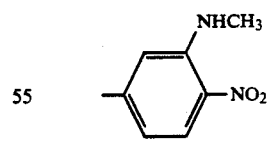

which may originate from the following dye:

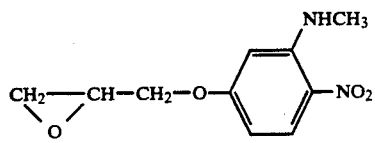

or

-continued

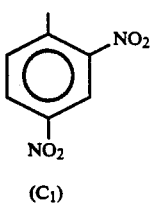 or 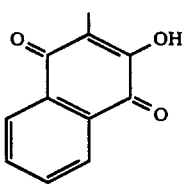

(C₁)                (C₂)

which originates, for (C₁), from 2,4-dinitro-1-chlorobenzene or from 2,4-dinitro-1-fluorobenzene, which can react with the amino functions of the protein with elimination of hydrochloric acid or hydrofluoric acid, respectively, and, for (C₂), from 2,3-dichloro-1,4-naphthoquinone, which can react with the amino functions of the protein with elimination of hydrochloric acid and hydrolysis of the second chlorine atom. Under these conditions, —X— is a direct bond and —T— is —NH—.

When Z denotes SR₃, it is preferred that P is 0 and R₄ is a hydrogen atom in the formulae (II) and (IV).

Chemically modified protein derivatives of formula (I) may be prepared as follows. The starting protein may optionally be subjected to acid hydrolysis or enzymatic hydrolysis, so that the molecular weight of the hydrolyzate obtained is from about 500 to 50,000.

The grafting of the residues of molecules of dye onto the protein molecule is carried out by reacting all or part of the amino, alcohol or thiol groups of the protein with one or more compounds of formula:

Y—X' wherein Y has the same meaning as above and X' is a reactive group containing one or more nucleofuges or one or more activated double bonds.

Then, optionally, if any available amine groups remain after the chemical grafting of the molecules of dye, an N-alkylation phase is carried out using an alkylating agent of the formulae:

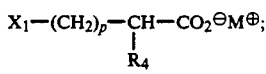    (II$_a$)

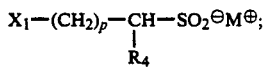    (III$_a$)

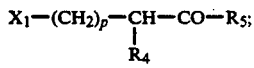    (IV$_a$)

or

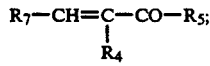    (IV'$_a$)

wherein X₁ is a halogen atom, R₄, R₅ and p have the same meaning given above and R₇ is a hydrogen atom or an alkyl group of 1 to 4 carbon atoms.

After this, if the protein used contains cysteine, either all or part of the disulphide bridges of the cysteine groups may be oxidized in the protein so as to obtain acid —SO₃H groups. This oxidation is optionally followed by salification of the above-mentioned acid —SO₃H groups. Alternatively, all or part of the disulphide bridges of the cysteine groups are reduced in the protein so as to obtain thiol groups, this reduction being followed by S-alkylation using an alkylating agent of the formulae (II$_a$), (III$_a$), (IV$_a$) and (IV'$_a$) defined above.

X' may be chosen from those described in "The Chemistry of Synthetic Dyes", Vol. VI, pages 1 to 209 (Ed. K. Venkataraman, Academic Press, New York, 1972).

If Y is a residue of an azo dye, an anthraquinone dye or a phthalocyanin derivative of the formulae given in "Color Index" (3rd Edition, Volume 3, pp. 3391 to 3560 [1971] and revised 3rd Edition, Volume 6, pp. 6265 to 6345 [1975]) under the designation "reactive", X' may be:

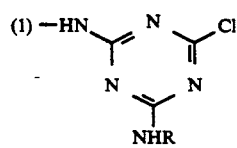

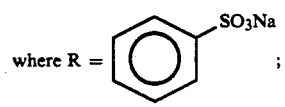

(2) —SO₂—CH₂—CH₂—OSO₃Na;

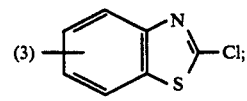

(4) —SO₂—NH—CH₂—CH₂—OSO₃N$_a$;

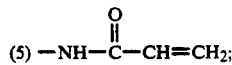

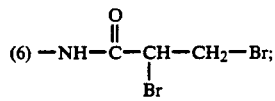

or

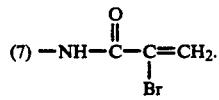

If Y is a residue of a dye possessing a carboxylic acid function or sulphonic acid function, such as, for example, the residue of a dye of the formulae:

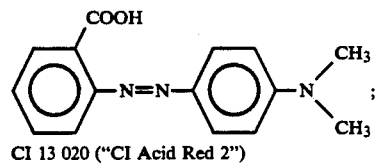

Cl 13 020 ("CI Acid Red 2")

or

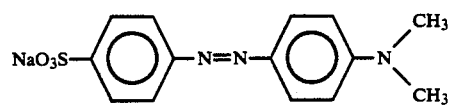

-continued

CI 13 025 ("CI Acid Orange 52")

X' is, respectively,

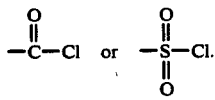

If Y is a residue of a dye possessing a 2,3-epoxy-1-propyloxy function, for example, the residue of a dye of the formula:

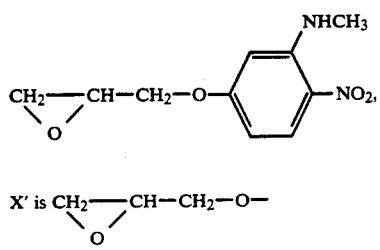

X' is CH₂——CH—CH₂—O—
       \\O/

If Y—X— is represented by:

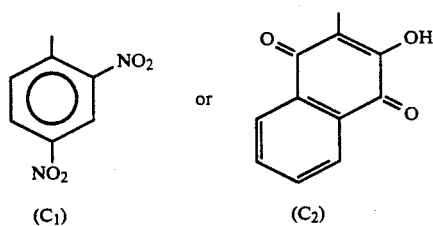

it is seen that Y—X' is, respectively,

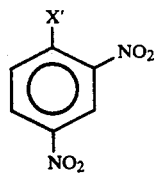

where X'=Cl or F, or

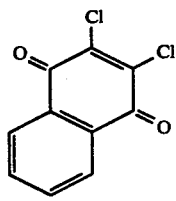

which is converted in alkaline medium at the time of grafting onto the protein to

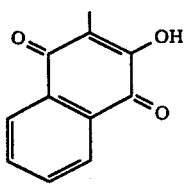

The process for the preparation of the protein derivative incorporates successive phases, namely an optional first hydrolysis phase, a second chemical grafting phase, optionally a third phase of N-alkylation, and optionally a fourth phase, either of oxidation or of S-alkylation on reduced —SH groups. The order of the phases 2, 3 and 4 can be transposed.

The optional first phase of the preparation process can be a conventional acid hydrolysis or an enzymatic hydrolysis using proteolytic enzymes, for example proteinase "PSF 2019", pronase, trypsin and papain. The working conditions, for example the pH and enzyme/-substrate ratio for the hydrolysis vary according to the enzyme used.

The second phase of the preparation process consists in particular in grafting compounds bearing chromophoric or chromogenic groups onto the amino, alcohol or thiol sites of the protein. These compounds possess a reactive group containing one or more nucleofuges or alternatively one or more activated double bonds which permit grafting by addition or nucleophilic substitution. The grafting may be performed in a conventional manner under variable pH conditions, according to the nature of the reactive group and of the protein.

The third optional phase of the preparation process may consist in an N-alkylation using an alkylating agent of formulae (II$_a$), (III$_a$), (IV$_a$) or (IV'$_a$) given above. The N-alkylating agent used advantageously may have the formula: $X_1$—$CH_2$—$CO_2^-M^+$, $X_1$ and $M^+$ having the meaning given above. The preferred N-alkylating agent is monochloroacetic acid.

The optional fourth phase of the process can consist either of oxidation of the disulphide bonds of the cysteine groups of the protein, or else of S-alkylation of the —SH groups obtained by prior reduction of the disulphide bridges of the protein by a solution of a reducing agent, an alkali metal thioglycolate or ammonium thioglycolate.

Oxidation of the protein which has undergone the above treatment or treatments converts cysteine groups of the protein to cysteic acid groups. This oxidation is advantageously carried out in acid medium using an oxidizing agent such as hydrogen peroxide or a peracid. The oxidation can optionally be followed by a salification of the —SO₃H group.

S-alkylation is carried out using an alkylating agent, preferably of formulae (II$_a$), (III$_a$), (IV$_a$) or (IV'$_a$) given above, the preferred agents and the especially preferred agent being those given in relation to the N-alkylation.

The color of the keratin derivatives of formula (I) depends on the nature of the molecule of dye grafted.

The proportions of the compounds or compounds of formula (I) in the compositions according to the invention vary according to the nature of the molecule of dye grafted onto the protein and to the intensity of the coloration sought for the composition. In the composition according to the invention, the compound or compounds of formula (I) may be dissolved in a solvent, for example water, a lower monoalcohol or polyol or an aqueous-alcoholic mixture. The preferred mono- or polyalcohols are ethanol, isopropanol, propylene glycol or glycerin. The compounds of formula (I) can also be dispersed in non-aqueous supports.

If the compositions according to the invention are intended for temporary coloring keratin fibers such as human hair and nails, especially human hair, the colored proteins are generally present in a proportion of from 0.005% to 10%, and preferably of from 0.02% to 8%, by weight relative to the total weight of the composition. The pH of the composition is preferably from 5 to 11, and more preferably from 6 to 10. The compositions according to the invention used in this manner are preferably applied for 1 to 45 minutes, more preferably 5 to 30 minutes, although for lotions applied as a hair rinse, there is not treatment time, the said lotions being applied and then dried.

The compositions according to the invention can also be used in the form of colored lacquers, optionally in aerosol form using a propellent.

The compositions according to the invention can be used in direct dyeing and can contain, in addition to the colored proteins, other colorants, in particular direct dyes such as azo dyes, anthraquinone dyes, nitrated dyes of the benzene series, 2,5-diaminoquinones, indophenols, indoanilines and indamines.

The compositions according to the invention can also contain alkalization or acidification agents and/or solvents and/or polymers and/or treatment products of cationic character and/or amides and/or thickeners and/or surfactants and/or additives commonly used in capillary cosmetics, such as sun filters, optical blues, antioxidants, sequestering agents and perfumes.

The alkalization agents which may be present in the compositions according to the invention can be, for example, mono- or triethanolamine, ammonia, sodium phosphate or sodium carbonate. The acidification agents which may be present in the composition according to the invention can be, for example, phosphoric, hydrochloric, lactic, tartaric, acetic or citric acid. These alkalization or acidification agents are intended for adjusting the pH of the tinctorial composition to the desired value.

The solvents present in the compositions according to the invention may be alcohols of 2 to 4 carbon atoms, such as ethyl or isopropyl alcohol or glycols such as ethylene glycol, propylene glycol, or butylene glycol, or glycol ethers such as the methyl, ethyl or butyl ether of ethylene glycol. The solvent is preferably present in an amount of from 0.5 to 50% by weight, preferably from 1 to 15% by weight, relative to the total weight of the composition.

The polymers which may be present in the composition are cosmetically acceptable polymers known to the specialist.

These polymers may be used at concentrations of from 0.1 to 4% by weight, preferably from 0.3 to 2% by weight, relative to the total weight of the composition.

The amides which may be present in the compositions according to the invention can be mono- or diethanolamides of fatty acids, optionally oxyethyleneated.

The thickeners may be cellulose derivatives such as carboxymethylcellulose, hydroxypropylmethylcellulose and hydroxyethylcellulose.

The surfactants may be anionic, cationic, non-ionic or amphoteric surfactants, such as sulphates, ether sulphates, fatty alcohol sulphonates, oxyethyleneated fatty acids or alcohols, oxyethyleneated alkylphenols, amines and quaternary ammonium salts.

The compositions according to the invention may be in many forms, for example in the form of a gel, cream, foaming liquid or milky liquid, and can be packaged in, for example, bottles, tubes or aerosols.

If compositions according to the invention are treatment and/or make-up products for the skin surface, the colored protein derivatives have the function of coloring the composition itself or the skin surface, and they can simultaneously confer on the latter the treatment effect and protection effect due to the presence of the protein chains.

The compositions according to the invention intended for application to the skin preferably contain the compound or compounds of formula (I) in an amount of from 0.01 to 10% by weight, relative to the total weight of the composition.

The cosmetic make-up compositions according to the invention may, for example, take the form of sticks, pastes, emulsions, suspensions, dispersions, powders or solutions, and may form lipsticks, mascaras, lip glosses, blushers, eye shadows, make-up foundations, eyeliners or powders.

The colored protein can be associated with inorganic or organic pigments, and especially with lacquers such as those commonly used.

The inorganic pigments are, in general, iron oxides (red, brown, black and yellow), chromium oxides, the ultramarines (aminosilicate polysulphides), titanium dioxide, manganese pyrophosphate and Prussian Blue (ferric ferrocyanide). These various compounds alone or mixed together are generally employed at concentrations of from 0.1 to 40% by weight with respect to the total weight of the cosmetic composition.

These compositions can also contain agents imparting pearlescence such as bismuth oxychloride, titanium mica and guanine crystals.

When the compositions take the form of sticks, especially lipstick, eye shadow, blusher and make-up foundation, a significant part of the compositions may consist of a fatty substance which can comprise one or more waxes, for example ozokerite, lanolin, lanolin alcohol, hydrogenated lanolin, acetylated lanolin, lanolin wax, beeswax, candellila wax, microcrystalline wax, carnauba wax, cetyl alcohol, stearyl alcohol, cocoa butter, lanolin fatty acids, petrolatum, vaselines, mono-, di- and triglycerides solid at 25° C., fatty esters solid at 25° C., silicone waxes such as methyloctadecane-oxypolysiloxane and poly(dimethyl-siloxy) stearoxysiloxane, stearic acid monoethanolamide, colophony and its derivatives such as glycol abietate and glycerol abietate, hydrogenated oils solid at 25° C., sucroglycerides, and calcium, magnesium, zirconium and aluminum oleates, myristates, lanolates, stearates or dihydroxystearates.

The fatty substance may also consist of a mixture of at least one wax and at least one oil, for example: paraffin oil, purcellin oil, perhydrosqualene, sweet-almond oil, avocado oil, oil of calophyllum, castor oil, sesame oil, jojoba oil, mineral oils having a boiling point between 310° and 410° C., silicone oils such as dimethylpolysiloxanes, linoleyl alcohol, linolenyl alcohol, oleyl alcohol, the oil of cereal seeds such as wheatgerm oil, isopropyl lanolate, isopropyl palmitate, isopropyl myristate, butyl myristate, cetyl myristate, hexadecyl stearate, butyl stearate, decyl oleate, acetylglycerides, octanoates and decanoates of such alcohols and polyalcohols as glycol and glycerol, the ricinoleates of alcohols and polyalcohols such as cetyl ricinoleate, isostearyl alcohol, isocetyl lanolate, isopropyl adipate, hexyl laurate or octyldodecanol.

In general, the fatty substance in these compositions in stick form may represent up to 99.9% by weight of the total weight of the composition.

The compositions may also contain other ingredients such as glycols, polyethylene glycols, polypropylene glycols, monoalkanolamides, uncolored polymers, inorganic or organic fillers, preservatives, UV filters or other additives common in cosmetics.

The compositions in stick form may contain a quantity of water, generally not exceeding 40% relative to the total weight of the cosmetic composition.

When the cosmetic compositions according to the invention are semi-solid in form, that is, in the form of pastes or creams, they may be used as a mascara, an eyeliner, a make-up foundation, a blusher, an eye shadow, a lipstick, or a concealer.

These pastes or creams may be emulsions of the water-in-oil or oil-in-water type, in which the fatty phase preferably represents from 1 to 98.8% by weight and the water phase preferably represents from 1 to 98.8% by weight and the emulsifier preferably represents from 0.1 to 30% by weight.

These compositions can also contain other conventional ingredients such as perfumes, antioxidants, preservatives, gelling agents, UV filters, colorings, pigments, agents imparting pearlescence, uncolored polymers and inorganic or organic fillers.

When the compositions take the form of a powder, they may consist essentially of an inorganic or organic filler such as talc, kaolin, starches, polyethylene powders or polyamide powders, as well as additives such as binders, colorings and the like.

Such compositions can also contain various additives commonly used in cosmetics such as perfumes, antioxidants and preservatives.

The present invention is further illustrated in detail in the following examples. These examples are included for illustrative purposes and should not be considered to limit the present invention.

EXAMPLE 1

Preparation of a colored protein derivative of formula (I), in which formula the proportion of units B is nil, the proportion of units A is approximately 61% by weight, M denotes hydrogen and unit A has the formula:

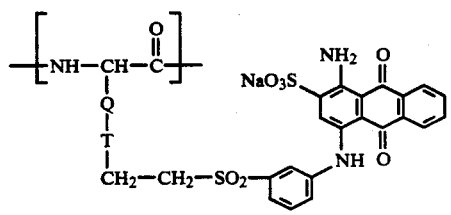

Q denoting alkyl, aryl or aralkyl groups of the amino acids of the protein, and T denoting NH or O or S.

The protein derivative on which the grafting is performed is a keratin hydrolyzate.

First stage: Hydrolysis of the keratin a) A suspension of 100 g of chicken feathers is brought to reflux in the course of 1 hour in 2 liters of dimethylformamide and 0.8 liter of water. The mixture is filtered hot and the treated feathers are washed with 2 liters of water and dried in the air.

b) 100 g of treated feathers are suspended in 2 liters of water. The pH is adjusted to 8.6-9.0, and the temperature is adjusted to 40° C. 3.5 g of enzyme PSF 2019 are added. The pH is maintained between 8.5 and 8.8 by adding 3% strength caustic soda. After addition of 1 liter of 3% strength caustic soda, the pH is allowed to fall to 8.45 and is then adjusted to pH 7 with dilute hydrochloric acid. The mixture is heated at 95° C. for 5 minutes to inactivate the enzyme, and is then allowed to return to room temperature. A little insoluble material is filtered off and the filtrate is lyophilized. 50 to 60 g of keratin hydrolyzate is obtained in the form of a beige powder.

The content of free amines is 2 meq/g.

Second stage: Grafting of the dye

The following are heated to 40° C.:

5 g of keratin hydrolyzate obtained as above
20 cm³ of water
20 cm³ of acetone
1N caustic soda, in sufficient quantity to bring the pH to 9.

There are added, in the course of 2 hours, 10 g of REMAZOL ® BRILLIANT BLUE R (CI No. 61 200) at 50% strength, which has the following structure:

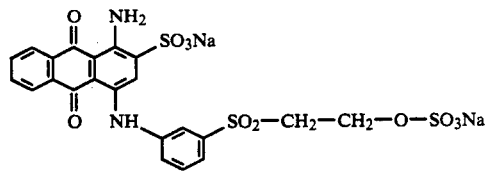

The pH is maintained between 8.8 and 9.2 by adding 1N caustic soda.

The mixture is stirred for 2 hours after the end of the addition of dye, and is then diluted with 150 cm³ of water. The pH is adjusted to 3 by adding concentrated hydrochloric acid. The colored protein precipitates. It is filtered off, washed 8 times with 150 cm³ of water and dried in the air.

5 g of colored keratin are obtained in the form of a blue powder possessing the following characteristics:

$\lambda_{max}$=594 nm (measured in an aqueous solution containing 1% colored protein)

percentage of grafted dye=61%

EXAMPLE 2

Preparation of a colored protein derivative of formula (I), in which formula the proportion of units B is nil, the proportion of units A is approximately 68% by weight, M denotes hydrogen and unit A has the formula:

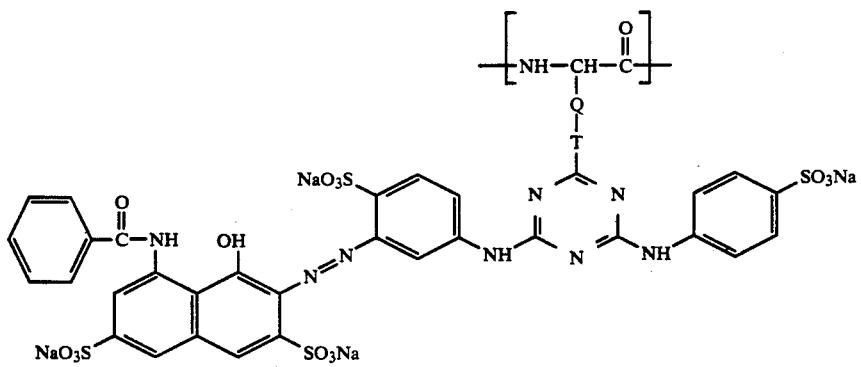

Q denoting alkyl, aryl or aralkyl groups of the amino acids of the protein, and T denoting NH or O.

The protein derivative on which the grafting is performed is a casein hydrolyzate.

First stage: Hydrolysis of the casein 100 g of nutrient casein is suspended in 1 liter of water. The pH is adjusted to between 1.8 and 2.0 by adding 35% strength hydrochloric acid. After the temperature has stabilized at 38°±1° C., 0.2 g of SIGMA ® pepsin 1:60,000 is added. Stirring is maintained for 8 hours at this temperature, and the enzyme is then inactivated at pH 8-8.5 for 10 hours. The solution is ultrafiltered so as to remove inorganic salts and the fraction of molecular mass below 1000. After lyophilization, there are obtained 85 g of hydrolyzate possessing an amine content of 2.54 meq/g.

Second stage: Grafting of the dye

The following are heated to 40° C.:
5 g of casein hydrolyzate obtained as above
25 cm³ of water
25 cm³ of acetone 1N caustic soda in sufficient quantity to bring the pH to 9.

There are added, in the course of 1 hour and 30 minutes, 11.8 g of CIBACRON ® BRILLIANT RED 3 BA (CI No. 18,105), which has the following structure:

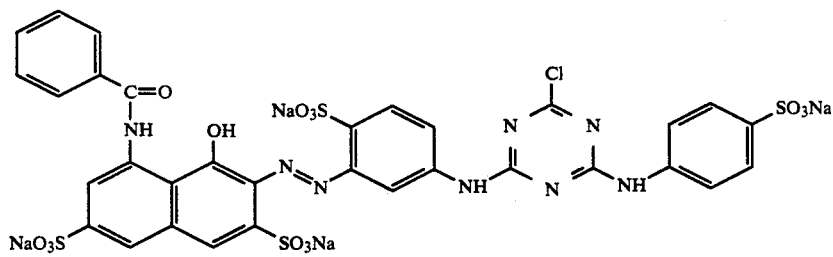

The pH is maintained between 8.8 and 9.2 by addition of 1N caustic soda.

The mixture is stirred for 4 hours after the end of the addition of the dye. The pH is adjusted to 2.2 by adding 2N hydrochloric acid. The colored protein precipitates. The product is filtered, washed copiously with water and dried in the air.

There are obtained 4.5 g of colored casein in the form of a red powder possessing the following characteristics:

$\lambda_{max}$=517 nm (measured in an aqueous solution containing 1% color protein)

Percentage of grafted dye=68%.

EXAMPLE 3

Preparation of a colored protein derivative of formula (I), in which formula the proportion of units B is nil, the proportion of units A is approximately 34% by weight, M denotes Na and unit A has the formula:

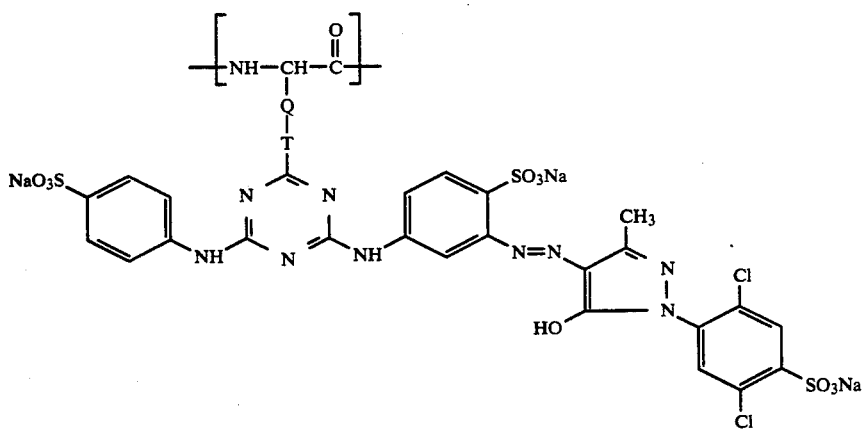

Q denoting alkyl, aryl or aralkyl groups of the amino acids of the protein and T denoting NH or O or S.

The protein derivative on which the grafting is performed is a keratin hydrolysate The following are heated to 45° C.:
10 g of the keratin hydrolysate obtained in the first stage of Example 1
50 cm³ of water
50 cm³ of acetone
30% strength caustic soda in sufficient quantity to bring the pH to between 8.5 and 9.5.

There are added, in the course of 2 hours, 10.3 g of CIBACRON ® BRILLIANT YELLOW 3 G-P (CI No. 18,972) which has the following structure:

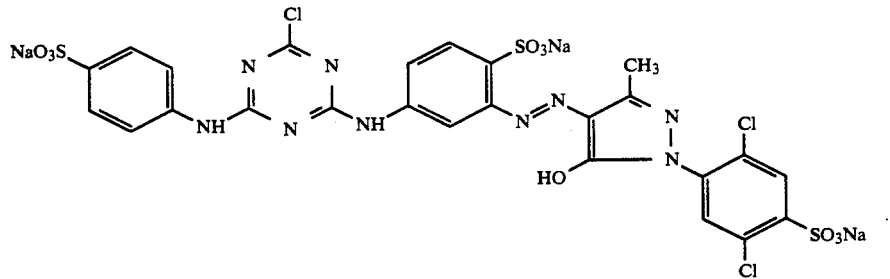

The pH is maintained between 8.5 and 9.5 by addition of 30% strength caustic soda.

The mixture is stirred for 1 hour at 45° C. after adding the dye, and the reactants are then left in contact overnight at room temperature.

The reaction mixture is adjusted to pH 3 by adding concentrated hydrochloric acid. It is filtered and the precipitate is washed copiously with water and then redissolved at pH 7.5 by adding caustic soda.

After lyophilization, there are obtained 3 g of colored keratin in the form of a yellow powder possessing the following characteristics:

$\lambda_{max}$ = 403 nm (measured in aqueous solution containing 1% of colored protein)
Percentage of grafted dye = 34%.

EXAMPLE 4

Preparation of a colored protein derivative of formula (I), in which formula the proportion of units B is nil, the proportion of units A is approximately 10% by weight, M denotes hydrogen and unit A has the formula:

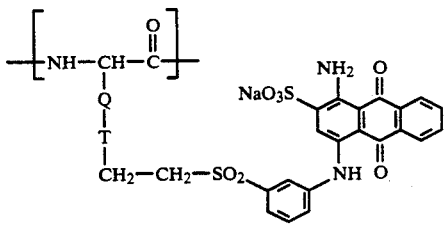

Q denoting alkyl, aralkyl or aryl groups of the amino acids of the protein and T denoting NH or O.

The protein derivative on which the grafting is performed is a gelatin hydrolyzate.

This protein derivative is obtained according to the procedure described in Example 1, in which the keratin hydrolyzate is replaced by gelatin ASF ROUSSELOT, which possesses an amine content of 1.7 meq/g.

The blue powder obtained possesses the following characteristics:

$\lambda_{max}$ = 596 m (measured in aqueous solution containing 1% colored protein)
Percentage of grafted dye = 62%.

EXAMPLE 5

Preparation of a colored protein derivative of formula (I), in which formula the proportion of units B is nil, the proportion of units A is approximately 16% by weight, M denotes Na and unit A has the formula:

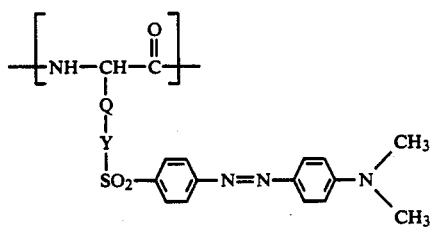

Q denoting alkyl, aryl or aralkyl groups of the amino acids of the protein, and T denoting NH.

The protein derivative on which the grafting is performed is a gelatin hydrolyzate.

9.03 g of gelatin ASF ROUSSELOT are dissolved in 35 cm³ of water and 35 cm³ of acetone. The pH of the solution is adjusted to 9.5 by means of 4N caustic soda. 4.8 g of 4-chlorosulphonyl-4'-(dimethylamino)azobenzene are introduced slowly while maintaining the pH of the reaction medium between 9 and 9.5 by adding 4N caustic soda. The reaction is allowed to continue for 15 hours at room temperature, and the acetone is then distilled off under reduced pressure. The aqueous solution thus obtained in dialyzed and then lyophilized. There are obtained 5.2 g of colored gelatin in the form of an orange powder which possesses the following characteristics:

$\lambda_{max} = 445$ nm (measured in a N/10 solution of NaOH containing 1% colored protein)

Percentage of grafted dye = 16%.

EXAMPLE 6

Preparation of a colored protein derivative of formula (I), in which formula the proportion of units B is nil, the proportion of units A is approximately 12% by weight, M denotes $(CH_3CH_2)_3N^+H$ and unit A has the formula:

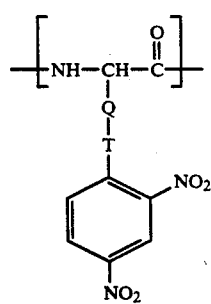

Q denoting alkyl, aryl or aralkyl groups of the amino acids of the protein and T denoting NH.

A protein derivative on which the grafting is performed is a gelatin hydrolyzate.

A solution containing 20 g of gelatin ASF ROUSSELOT, 6.16 g of 2,4-dinitro-1-fluorobenzene and 5.32 cm³ of triethylamine in 80 cm³ of water and 80 cm³ of acetone is heated under reflux for 2 hours and 30 minutes. After being cooled, the reaction mixture is poured into 500 cm³ of acetone. The gummy precipitate is washed with acetone, then ground and dried. There are obtained 17.5 g of colored gelatin in the form of a yellow powder which possesses the following characteristics:

$\lambda_{max} = 340$ nm (measured in a N/10 solution of NaOH containing 1% colored protein).

Percentage of grafted dye = 12%.

EXAMPLE 7

Preparation of a colored protein derivative of formula (I) in which formula the proportion of units B is nil, the proportion of units A is approximately 5% by weight, M denotes hydrogen and unit A has the formula:

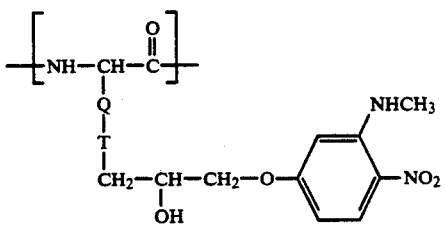

Q denoting alkyl, aryl or aralkyl groups of the amino acids of the protein and T denoting NH or O.

The protein derivative on which the grafting is performed is a gelatin hydrolyzate.

A suspension of 8.16 g of gelatin ASF ROUSSELOT and 2.75 g of 1-epoxypropyloxy-3-methylamino-4-nitrobenzene in 130 cm³ of ethanol containing 1.9 cm³ of triethylamine is heated for 8 hours at 80° C. At the end of the reaction, the ethanol is distilled off under reduced pressure. The residue is redissolved in 50 cm³ of water. The pH of the solution is adjusted to 2 by means of dilute hydrochloric acid. The solution is poured into 200 cm³ of acetone. The gummy precipitate is washed with acetone, and then ground and dried under vacuum. There are obtained 7 g of colored gelatin in the form of a yellow powder which possesses the following characteristics:

$\lambda_{max} = 428$ nm (measured in a N/10 solution of NaOH containing 1% colored protein).

Percentage of grafted dye = 5%.

EXAMPLE 8

Preparation of a colored protein derivative of formula (I), in which formula the proportion of units B is nil, the proportion of units A is approximately 14% by weight, M denotes hydrogen and unit A has the formula:

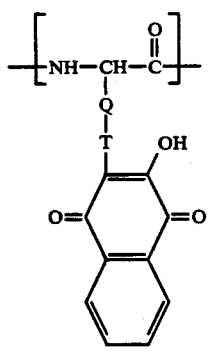

Q denoting alkyl, aryl, or aralkyl groups of the amino acids of the protein and T denoting NH.

The protein derivative on which the grafting is performed is a gelatin hydrolyzate.

6.02 g of gelatin ASF ROUSSELOT, 1.14 g of 2,3-dichloro-1,4-naphthoquinone in 30 cm³ of ethanol and 5 cm³ of water containing 1.01 g of triethylamine are heated for 5 hours at 80° C. The reaction mixture is concentrated under reduced pressure. The residue is taken up in 150 cm³ of water and the solution is adjusted to pH 4.2 with dilute hydrochloric acid. The gummy precipitate is washed with water and then acetone, ground and dried. There are obtained 3.03 g of colored gelatin in the form of a brown powder possessing the following characteristics:

$\lambda_{max}$=465 nm (measured in a N/10 solution of NaOH containing 1% colored protein)

Percentage of grafted dye=14%.

EXAMPLE 9 (comparative)

The intensity of the coloration and the resistance of this coloration to washing of permanent gray hair dyed with a composition containing a colored protein in accordance with the present invention and with a composition containing a polymer (polyaspartic) colored in accordance with U.S. Pat. No. 4,314,808 to Jacquet et al were evaluated.

The dye products employed in both these compositions contain an anthraquinone moiety and had the following formulas.

1. Colored polymer of Example 2 of U.S. Pat. No. 4,314,808 has the formula:

$$\left[\begin{array}{c}HN-C_2H_3-CO\\ |\\ CO\\ |\\ H-N-(CH_2)_3-NH\\ \\ CH_3HN\end{array}\right]_a \left[\begin{array}{c}NH-C_2H_3-CO\\ |\\ CO\\ |\\ NH\\ |\\ (CH_2)_3\\ |\\ \oplus N\\ / \backslash \\ H_3C \quad CH_3\\ CH_3\end{array}\right]_c$$

$CH_3SO_4^{\ominus}$ wherein the ratio of a/c=20/80.

This formula is based on the general formula where R=H, x=3, $X_1$ is an anthraquinone residue, R'''=H, y=3, $$Y = {}^+N{-}R''$$
with R' and R''' branches wherein R', R" and R'''=CH₃, and b=d=0.

2. Colored protein of Example 1 has formula I wherein the amount of the B units is zero, the amount of the A units is about 61 weight percent, M⁺=H and unit A has the formula:

[—NH—CH—C(=O)+]
     |
     Q
     |
     T
     |
     CH₂CH₂—SO₂—(phenyl)—NH—(anthraquinone with NaO₃S, NH₂)

wherein

Q represents the alkyl, aryl or arylalkyl group of the amino acid of hydrolized keratin and T represents NH, O or S. That two hair setting lotion compositions having essentialy the formulation given in Example C₁ of U.S. Pat. No. 4,314,808 were prepared.

COMPOSITION A

Prior art composition—essential reproduction of Example C₁ of U.S. Pat. No. 4,314,808

| | |
|---|---|
| Colored polymer - formula 1, above | 0,5 g |
| Vinyl pyrrolidone/vinyl acetate copolymer, (60/40) | 0.5 g |
| "Gafquat 734" - quaternized polyvinyl pyrrolidone | 0.4 g |
| Alkyl dimethylhydroxy ethyl ammonium bromide wherein the alkyl is the residue of tallow | 0.2 g |
| Ethyl alcohol | 50 cc |
| Water, sufficient amount for pH = 6.5 | 100 cc |

COMPOSITION B

Composition employing a colored protein in accordance with/present invention

This composition is essentially identical to that of composition A, above, except that the colored polymer in Composition A is replaced by the same amount of the colored protein of formula 2, above.

The samples of permanent gray hair are immersed in these dye solutions, using 7 cc of solution per gram of hair. They are then permitted to remain in contact with the dye solutions for a period of 5 minutes at ambient temperature. The samples are then drained and dried.

Their color is determined in accordance with the Munsell system.

According to this system, a color is determined in a three dimensional system by three parameters, H, V and C.

1. The shade or hue is designated H. There exist 10 shades: R, YR, Y, GY, G, BG, B, PB, P and RP (these initials represent the following: R for Red, Y for Yellow, G for Green, B for Blue, P for Purple. The intermediates, YR=yellow red or orange, etc.) In each base shade, the perceptible shades are designated by a number ranging from 0 to 10, for example 2B, 5PB.

The number 10 for a shade or hue corresponds to a number 0 for the succeeding hue or shade. For example,

10B=0PB

10PB=0P, etc.

These different hues appear on a circle called "Rosace de Munsell".

2. With regard to the brightness or V value, black corresponds to a theoretical brightness of 0 while white corresponds to a brightness of 10.

3. Concerning the purity of chroma, C, this parameter permits an evaluation of the saturation of a color. The higher the chroma value, the greater the color is lively or intense. The smaller the chroma value, the more the color is dull and gray.

To evaluate the extent of dyeing of the samples, the color of the nondyed sample is compared to that of the dyed sample and the difference in color is calculated by applying the Nickerson equation:

$$E = 0.4 Co\, dH + 6 dV + 3 dC$$

The greater the difference, the higher is the extent of dyeing of the hair.

Co represents the chroma of the nondyed sample taken as a reference.

dH, dV and dC are the absolute values of the variation of the hue (H), brightness (V) and purity or chroma (C).

The color of the nondyed sample is 4.55Y 5.7/1.5.

The following results were achieved:

| Composition | Color of dyed sample | ΔE |
|---|---|---|
| A (prior art) | 0.95 B 4.5/1.3 | 29.6 |
| B present invention | 9.55 B 4.4/1.9 | 36.0 |

The sample thus dyed were then submitted to a washing procedure under strictly identical conditions.

There was employed an apparatus consisting of a plate thermostated at 26°±0.5° C., a roller provided with a back and forth movement (20 movements per minute) and a system permitting the delivery of shampoo (with the aid of a precision burette) and water heated to 36°±0.5° C.

The sample is fixed to one end of the thermostated plate. 1.5 cc of shampoo are delivered to the plate and are distributed over the entire width of the plate.

60 passages of the roller are then effected.

Thereafter 240 cc of rinse water are delivered to the plate and 60 passages of the roller are carried out. 240 cc of water are again delivered and 80 passages of the roller are then effected. The sample is then dried.

The color is then determined in accordance with the Munsell system.

The color of the sample dyed with Composition A (prior art) and washed is 2.05 G 5.1/0.7.

The color of the sample dyed with Composition B according to the invention and washed is 9.45 Y 5.4/1.

It will be noted that Composition B according to the invention imparts to the hair a color which is more intense than that achieved with Composition A (prior art); that this color achieved with Composition B is nearly completely removed on washing since the shade of the washed sample is close to that of the nondyed sample which is not the case with the color achieved with Composition A (prior art).

In conclusion, the colored protein in accordance with the present invention imparts to hair an intense semipermanent color which can be easily removed on washing, whereas the colored polymer of the prior art imparts to hair a less intense color which is resistant to washing.

EXAMPLE 10

A setting lotion having the following composition is prepared:

| | |
|---|---|
| Compound of Example 1 | 0.1 g |
| Vinyl acetate/crotonic acid (90:10) copolymer | 1.8 g |
| Vinylpyrrolidone/vinyl acetate (60:40) copolymer | 0.4 g |
| Ethyl alcohol | qs 50° alcoholic strength |
| Triethanolamine | qs pH 7 |
| Demineralized water | qs 100 g |

This setting lotion is applied to brown hair. After drying and shaping, the hair has an ash-grey tone. The color is eliminated after one washing.

EXAMPLE 11

A lotion having the following composition is prepared:

| | |
|---|---|
| Compound of Example 2 | 0.05 g |
| Dye "CI 62 045" sold under the name "Bleu dimacide A 2 BL" by the Société "PCUK" | 0.04 g |
| 2-(β-Hydroxyethyl)amino-5-hydroxy-1-nitro-benzene | 0.02 g |
| Dye "CI 13 065" sold under the name "Jaune acétacide 4 R extra" by the Société "PCUK" | 0.02 g |
| Vinyl acetate/vinylpyrrolidone (30:70) copolymer | 0.6 g |
| Ethyl alcohol | 10 g |
| Propylene glycol | 1 g |
| Nonylphenol oxyethyleneated with 9 mol of ethylene oxide | 2 g |
| Triethanolamine | qs pH 7 |
| Demineralized water | qs 100 g |

This lotion is applied to dark chestnut-colored hair. The hair is dried and then has a copper-colored dark auburn tone. The coloration is eliminated after one washing.

EXAMPLE 12

A setting lotion having the following composition is prepared:

| | |
|---|---|
| Compound of Example 3 | 0.05 g |
| 2-(β-Hydroxyethyl)amino-4'-(N,N-bis-[β-hydroxyethyl]amino)-5-anilino-1,4-benzoquinone | 0.016 g |
| 3-(N-[2-Chloro-4-hydroxyphenyl]-N-acetyl-amino)-6-methoxy-1,4-benzoquinoneimine | 0.024 g |
| 3-(N-[3-Chloro-4-methylaminophenyl] ureido)-6-methyl-1,4-benzo-quinoneimine | 0.009 g |
| Vinyl acetate/crotonic acid (90:10) copolymer | 2.7 g |
| Vinylpyrrolidone/vinyl acetate (60:40) copolymer | 0.5 g |
| Ethyl alcohol | qs 50° alcoholic strength |
| Triethanolamine | qs pH 7 |
| Demineralized water | qs 100 g |

This setting lotion is applied to light chestnut-colored hair. After drying, the hair has a dark auburn-brown tone. The coloration is eliminated after one washing.

EXAMPLE 13

A temporary coloring product having the following composition is prepared:

| | |
|---|---|
| Compound of Example 2 | 0.05 g |
| Dye "CI 20 170" sold under the name "Brun clair sella acide RF" by the Société "CIBA GEIGY" | 0.015 g |
| Dye "CI 62 045" sold under the name "Bleu dimacide A 2 BL" by the Société "PCUK" | 0.02 g |
| Vinyl acetate/vinylpyrrolidone (30:70) copolymer | 0.6 g |
| Ethyl alcohol | 10 g |
| Propylene glycol | 1 g |
| Nonylphenol oxyethyleneated with 9 mol of ethylene oxide | 2 g |
| Triethanolamine | qs pH 7 |

-continued

| | |
|---|---|
| Demineralized water | qs 100 g |

This temporary coloring product is applied to light blond hair. After drying, the hair has a pearly beige tone.

EXAMPLE 14

A styling lotion having the following composition is prepared:

| | |
|---|---|
| Compound of Example 1 | 0.1 g |
| Compound of Example 2 | 0.05 g |
| Vinyl acetate/crotonic acid (90:10) copolymer | 2.7 g |
| Vinylpyrrolidone/vinyl acetate (60:40) copolymer | 0.5 g |
| Ethyl alcohol | qs 50° alcoholic strength |
| Triethanolamine | qs pH 7 |
| Demineralized water | qs 100 g |

This styling lotion is applied to light chestnut-colored hair. After drying, the hair has an ash-mauve tone. The coloration is eliminated after one washing.

EXAMPLE 15

A setting lotion having the following composition is prepared:

| | |
|---|---|
| Compound of Example 2 | 0.1 g |
| Vinyl acetate/crotonic acid (90:10) copolymer | 1.8 g |
| Vinylpyrrolidone/vinyl acetate (60:40) copolymer | 0.4 g |
| Ethyl alcohol | qs 50° alcoholic strength |
| Triethanolamine | qs pH 7 |
| Demineralized water | qs 100 g |

This setting lotion is applied to chestnut-colored hair. After drying and styling, the hair is shaded a dark auburn tone. The shade is eliminated after one washing.

EXAMPLE 16

A liquid composition having the following formulation is prepared:

| | |
|---|---|
| Compound of Example 1 | 0.03 g |
| Compound of Example 2 | 0.02 g |
| Dye "CI 62 045" sold under the name "Bleu dimacide A 2 BL" by the Société "PCUK" | 0.01 g |
| 2-($\beta$-Hydroxyethyl)amino-5-hydroxy-1-nitro-benzene | 0.01 g |
| Dye "CI 13 065" sold under the name "Jaune acétacide 4 R extra" by the Société "PCUK" | 0.02 g |
| Vinyl acetate/vinylpyrrolidone (30:70) copolymer | 0.6 g |
| Ethyl alcohol | 10 g |
| Propylene glycol | 1 g |
| Nonylphenol oxyethyleneated with 9 mol of ethylene oxide | 2 g |
| Triethanolamine | qs pH 7 |
| Demineralized water | qs 100 g |

This liquid composition is applied to natural or dyed dark blond hair. After drying, the hair is tinted a beige copper-colored tone which can be eliminated by one washing.

EXAMPLE 17

A lipstick having the following composition is prepared:

| | |
|---|---|
| Compound of Example 2 | 2 g |
| Castor oil | 65 g |
| Lanolin | 10 g |
| Isopropyl myristate | 5 g |
| Beeswax | 6 g |
| Carnauba wax | 3 g |
| Candellila wax | 3 g |
| Ozokerite | 3 g |

The oils and fatty substances are heated to about 60°–65° C., and at this temperature the colored protein is dispersed with vigorous stirring. After cooling, a magenta-colored stick is obtained.

EXAMPLE 18

A make-up foundation having the following composition is prepared:

| | |
|---|---|
| Compound of Example 3 | 1.5 g |
| Compound of Example 2 | 0.1 g |
| Lanolin fatty alcohols oxyethyleneated with 20 mol of ethylene oxide | 7 g |
| Triglycerides of coconut fatty acids | 30 g |
| Glycerol monostearate | 2 g |
| Silicone oil | 1.5 g |
| Cetyl alcohol | 1.5 g |
| Water | qs 100 g |

The colored proteins are dissolved in water containing the emulsifiers (oxyethyleneated lanolin fatty alcohols and glycerol monostearate).

The aqueous phase is heated to about 80° C.; the fatty phase, previously heated to 80° C., is added with vigorous stirring. The mixture is allowed to return to room temperature with moderate stirring.

A make-up foundation is obtained which can be applied readily and uniformly to the skin.

EXAMPLE 19

A setting lotion having the following composition is prepared:

| | |
|---|---|
| Compound of Example 6 | 0.14 g |
| Compound of Example 1 | 0.06 g |
| Compound of Example 2 | 0.08 g |
| Vinyl acetate/vinylpyrrolidone copolymer | 1.2 g |
| Ethyl alcohol | 15 g |
| Propylene glycol | 1 g |
| Triethanolamine | qs pH 7.5 |
| Demineralized water | qs 100 g |

Applied to light chestnut-colored hair, this setting lotion imparts, after drying, a dark chestnut color with dark auburn tones. The color is eliminated after one washing.

EXAMPLE 20

A make-up foundation having the following composition is prepared:

| | |
|---|---|
| Compound of Example 5 | 0.15 g |
| Compound of Example 7 | 1.1 g |
| Compound of Example 8 | 0.4 g |

| -continued | |
|---|---|
| Lanolin fatty alcohols oxyethyleneated with 20 mol of ethylene oxide | 7 g |
| Triglycerides of coconut fatty acids | 30 g |
| Glycerol monostearate | 2 g |
| Silicone oil | 1.5 g |
| Cetyl alcohol | 1.5 g |
| Water | qs 100 g |

The procedure is as described in Example 18. A make-up foundation which can be readily and uniformly applied to the skin is likewise obtained.

What is claimed is:

1. A process for the temporary coloring of human hair, nails or the skin comprising applying thereto in an amount effective to color said human hair, nails or skin a composition comprising a solution in water, a lower mono-alcohol or polyol or an aqueous alcoholic mixture wherein the alcohol is present in an amount ranging from 0.5 to 50 percent by weight of protein derivative having a molecular weight of from 500 to 50,000 and having the formula:

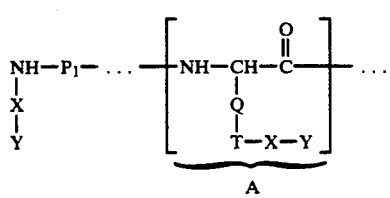

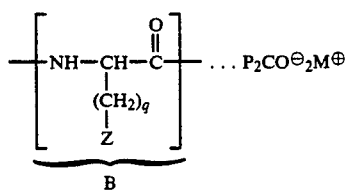

wherein

Y is a residue of a molecule of dye of formula YX' selected from the group consisting of CI 13245, CI 14824, CI 16202, CI 17865, CI 17756, CI 17757, CI 17910, CI 18096, CI 18097, CI 18105, CI 18156, CI 18157, CI 18159, CI 18852, CI 18972, CI 18990, CI 19036, CI 61200, CI 61210, CI 61211, CI 74460 and CI 74459, wherein X' is (1) 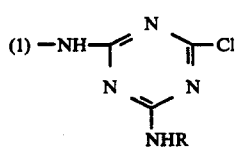

wherein R is (2) 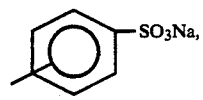

(2) —SO$_2$—CH$_2$—CH$_2$—OSO$_3$Na, (3) 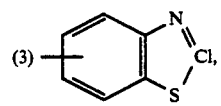

(4) —SO$_2$—NH—CH$_2$—CH$_2$—OSO$_3$Na, (5) 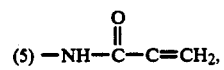

(6) 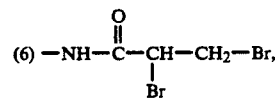

or (7) 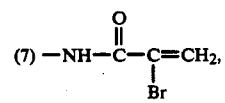

X is:

(1) 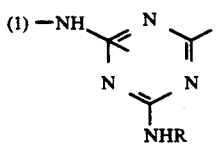

wherein R is:

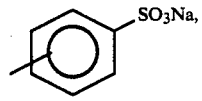

(2) —SO$_2$—CH$_2$—CH$_2$—, (3) 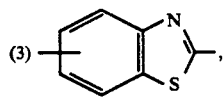

(4) —SO$_2$—NH—CH$_2$—CH$_2$—

(5) 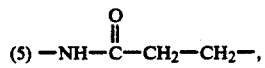

or (6) 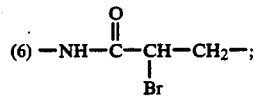

P$_1$ and P$_2$ are non-acylated chains of said protein which are not modified chemically by addition or nucleophilic substitution, said protein being selected from the group consisting of:
(1) a protein of animal origin selected from the group consisting of keratin, gelatin, egg albumin, blood serum albumin, casein and lactalbumin,
(2) a protein of vegetable origin selected from the group consisting of soya, groundnut and cotton seed, and (3) a hydrolyzate of the protein defined in (1) and (2), M is hydrogen, alkali metal, magnesium or $N^+(R_2)_4$, wherein each $R_2$ is, independently, hydrogen, alkyl having 1–4 carbon atoms or hydroxyalkyl having 1–4 carbon atoms, Q is an alkyl, aryl or aralkyl group of side chain of amino acid of unit A of said protein derivative, T is O, NH or S, Z is:
(1) $SO_3^-M^+$, wherein M has the meaning given above,
(2) $SR_3$, wherein
$R_3$ is

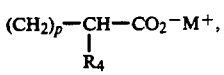

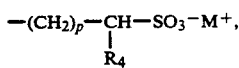

or

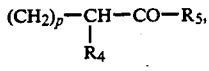

M has the meaning given above,
p is 0 or an integer from 1–5,
$R_4$ is hydrogen or alkyl having 1–4 carbon atoms and
$R_5$ is

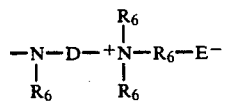

or

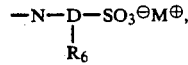

wherein D is linear or branched alkylene having 2–10 carbon atoms,

M has the meaning given above and each $R_6$ is, independently, hydrogen, alkyl having 1–4 carbon atoms, hydroxyalkyl having 1–4 carbon atoms and $E^-$ is a halide, $RCOO^-$, $RSO_3^-$ or $RSO_4^-$, wherein
R is a hydrocarbon group having 1–10 carbon atoms, or (3) an amino-terminal group from amino acid of unit B of said protein derivative, which amino acid is basic and is unsubstituted or mono- or disubstituted on the amino group with an $R_3$ group, wherein
$R_3$ is

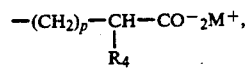

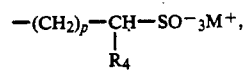

or

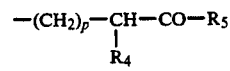

wherein p, $R_4$, M and $R_5$ have the meanings given above, with the proviso that Z is only $SO_3^-M^+$ or $SR_3$ when the amino acid of the unit B contains cysteine, q is an integer from 1 to 5 with the proviso that when Z is $SO_3^-M^+$ or $SR_3$, q is 1 and the amino acid of the unit B contains cysteine, the units A make up 1 to 70 percent by weight of said protein derivative, the units B make up 0 to 15 percent by weight of said protein derivative, and said protein derivative is present in an amount ranging from 0.005 to 10 percent by weight based on the total weight of said composition.

2. The process of claim 1 wherein said composition is applied to the skin and wherein said protein derivative is present in an amount ranging from 0.01 to 10 percent by weight based on the total weight of said composition.

3. The process of claim 1 wherein said protein derivative is present in an amount ranging from 0.02 to 8 percent by weight based on the total weight of said composition.

4. The process of claim 1 wherein said composition has a pH from 5 to 11.

5. The process of claim 1 wherein said composition has a pH of from 6 to 10.

6. A process for the temporary coloring of human hair, nails or the skin comprising applying thereto in an amount effective to color said human hair, nails or skin a composition comprising a solution in water, a lower mono-alcohol or polyol or an aqueous alcoholic mixture wherein the alcohol is present is an amount ranging from 0.5 to 50 percent by weight of a protein derivative having a molecular weight of from 500 to 50,000 and having the formula:

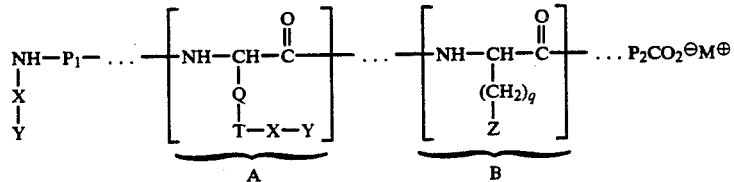

(I)

wherein

-continued

Y is 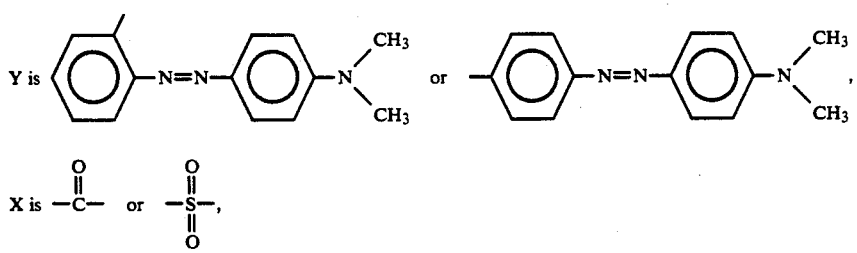

X is $-\overset{\overset{O}{\|}}{C}-$ or $-\overset{\overset{O}{\|}}{\underset{\underset{O}{\|}}{S}}-$, $P_1$ and $P_2$ are non-acylated chains of said protein which are not modified chemically by addition or nucleophilic substitution, said protein being selected from the group consisting of
(1) a protein of animal origin selected from the group consisting of keratin, gelatin, egg albumin, blood serum albumin, casein and lactalbumin,
(2) a protein of vegetable origin selected from the group consisting of soya, groundnut and cotton seed, and
(3) a hydrolyzate of the protein defined in (1) and (2), M is hydrogen, alkali metal, magnesium or $N^+(R_2)_4$, wherein each $R_2$ is, independently, hydrogen, alkyl having 1-4 carbon atoms or hydroxyalkyl having 1-4 carbon atoms, Q is an alkyl, aryl or aralkyl group of side chain of amino acid of unit A of said protein derivative, T is NH, Z is:
(1) $SO_3^-M^+$, wherein M has the meaning given above,
(2) $SR_3$, wherein $R_3$ is

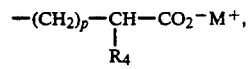

or

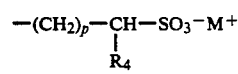

or

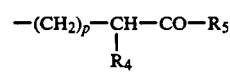

wherein M has the meaning given above, p is 0 or an integer from 1-5, $R_4$ is hydrogen or alkyl having 1-4 carbon atoms and $R_5$ is

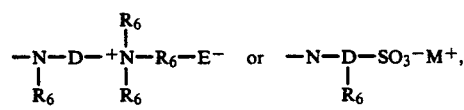

wherein D is linear or branched alkylene having 2-10 carbon atoms, M has the meaning given above and each $R_6$ is, independently, hydrogen, alkyl having 1-4 carbon atoms, hydroxyalkyl having 1-4 carbon atoms and $E^-$ is a halide, $RCOO^-$, $RSO_3^-$ or $RSO_4^-$, wherein R is a hydrocarbon group having 1-10 carbon atoms, or
(3) an amino-terminal group from amino acid of unit B of said protein derivative, which amino acid is basic and unsubstituted or mono- or disubstituted on the amino group with an $R_3$ group, wherein $R_3$ is

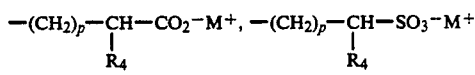

or

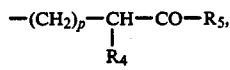

wherein p, $R_4$, M and $R_5$ have the meanings given above, with the proviso that Z is only $SO_3^-M^+$ or or $SR_3$ when the amino acid of the unit B contains cysteine, q is an integer from 1 to 5, with the proviso that when Z is $SO_3^-M^+$ or $SR_3$, q is 1 and the amino acid of the unit B contains cysteine, the units A make up 1 to 70 percent by weight of said protein derivative, the units B make up 0 to 15 percent by weight of said protein derivative, and said protein derivative is present in an amount ranging from 0.005 to 10 percent by weight based on the total weight of said composition.

7. A process for the temporary coloring of human hair, nails or the skin comprising applying thereto in an amount effective to color said human hair, nails or skin a composition comprising a solution in water, a lower mono-alcohol or polyol or an aqueous alcoholic mixture, wherein the alcohol is present in an amount ranging from 0.5 to 50 percent by weight of a protein derivative said protein derivative having a molecular weight of from 500 to 50,000 and having the formula:

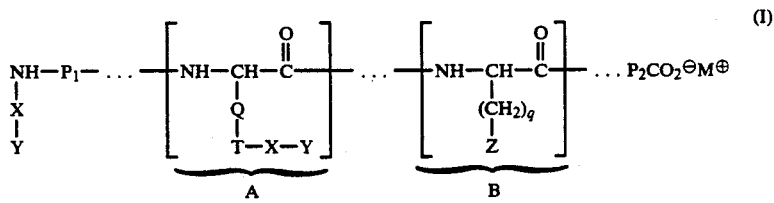

(I)

wherein

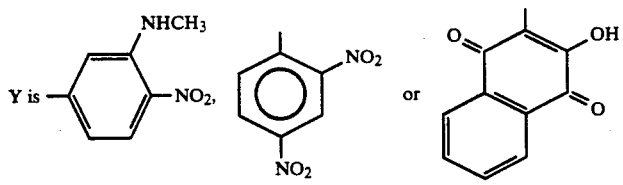

X is a direct bond or —CH$_2$—CHOH—CH$_2$—O—,

P$_1$ and P$_2$ are non-acylated chains of said protein which are not modified chemically by addition or nucleophilic substitution, said protein being selected from the group consisting of
(1) a protein of animal origin selected from the group consisting of keratin, gelatin, egg albumin, blood serum albumin, casein and lactalbumin,
(2) a protein of vegetable origin selected from the group consisting of soya, groundnut and cotton seed, and
(3) a hydrolyzate of the protein defined in (1) and (2), M is hydrogen, alkali metal, magnesium or N$^+$(R$_2$)$_4$ wherein each R$_2$ is, independently, hydrogen, alkyl having 1-4 carbon atoms or hydroxyalkyl having 1-4 carbon atoms, Q is an alkyl, aryl or aralkyl group of side chain of amino acid of unit A of said protein derivative, T is NH when X is a direct bond, or —NH— or —O— when X is —CH$_2$—CHOH—CH$_2$—O—, Z is an amino-terminal group from amino acid of unit B of said protein derivative, which amino acid is basic and unsubstituted or mono- or disubstituted on the amino group with an R$_3$ group, wherein R$_1$ is

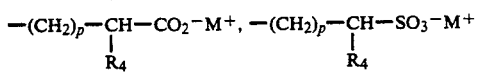

or

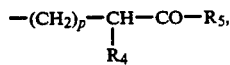

wherein M has the meaning given above, p is 0 or an integer from 1-5, R$_4$ is hydrogen or alkyl having 1-4 carbon atoms and R$_5$ is

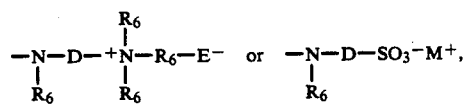

wherein D is linear or branched alkylene having 2-10 carbon atoms, M has the meaning given above and each R$_6$ is, independently, hydrogen, alkyl having 1-4 carbon atoms and hydroxyalkyl having 1-4 carbon atoms and E$^-$ is a halide, RCOO$^-$, RSO$_3^-$ or RSO$_4^-$ ion wherein R is a hydrocarbon group having 1-10 carbon atoms, q is an integer from 1 to 5, the units A make up 1 to 70 percent by weight of said protein derivative, the units B make up 0 to 15 percent by weight of said protein derivative, and said protein derivative is present in an amount ranging from 0.005 to 10 percent by weight based on the total weight of said composition.

8. A process for the temporary coloring of human hair, nails or the skin comprising applying thereto in an amount effect to color said human hair, nails or skin a composition comprising a solution in water, a lower mono-alcohol or polyol or an aqueous alcoholic mixture wherein the alcohol is present in an amount ranging from 0.5 to 50 percent by weight of a protein derivative having a molecular weight of from 500 to 50,000 and having the formula:

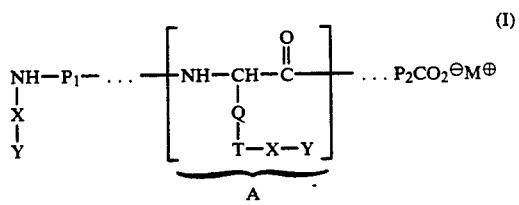

and being selected from the group consisting of
(1) a colored protein derivative having formula (I) given above wherein the unit A is approximately 61 percent by weight of said protein derivative, M represents hydrogen,
X-Y has the formula

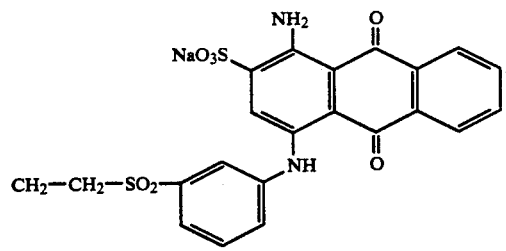

wherein
Q represents alkyl, aryl or aralkyl groups of amino acids of P$_1$ and P$_2$ wherein
P$_1$ and P$_2$ are non-acylated chains of a keratin hydrolyzate which are not modified chemically by addition or nucleophilic substitution, and
T represents NH, O or S;
(2) a colored protein derivative having formula (I) given above wherein the unit A is approximately 68 percent by weight of said protein derivative, M represents hydrogen and -XY has the formula:

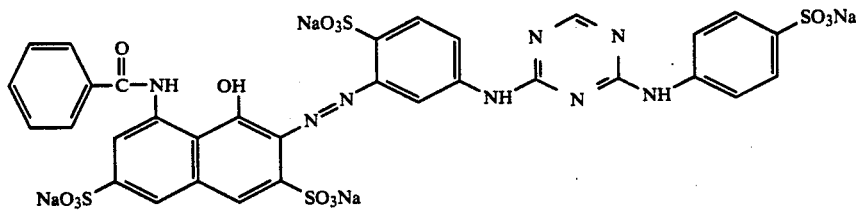

wherein
Q represents alkyl, aryl or aralkyl groups of amino acids of $P_1$ and $P_2$ wherein
$P_1$ and $P_2$ are non-acylated chains of a casein hydrolyzate which are not modified chemically by addition or nucleophilic substitution, and
T represents NH or O;
(3) a colored protein derivative having formula (I) given above wherein the unit A is approximately 34 percent by weight of said protein derivative, M represents Na and -XY has the formula:

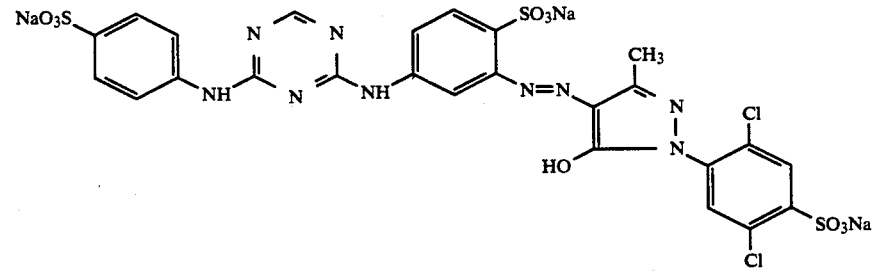

wherein
Q represents alkyl, aryl or aralkyl groups of amino acids of $P_1$ and $P_2$ wherein
$P_1$ and $P_2$ are non-acylated chains of a keratin hydrolyzate which are not modified chemically by addition or nucleophilic substitution, and
T represents NH, O or S;
(4) a colored protein derivative having formula (I) given above wherein the unit A is approximately 10 percent by weight of said protein derivative, M represents hydrogen and -XY has the formula:

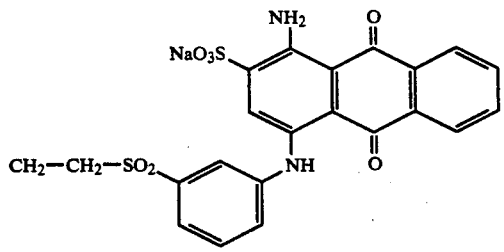

wherein
Q represents alkyl, aralkyl or aryl groups of amino acids of $P_1$ and $P_2$ wherein
$P_1$ and $P_2$ are non-acylated chains of a gelatin hydrolyzate which are not modified chemically by addition or nucleophilic substitution, and
T represents NH or O;
(5) a colored protein derivative having formula (I) given above wherein unit A is approximately 16 percent by weight of said protein derivative, M represents Na and -XY has the formula:

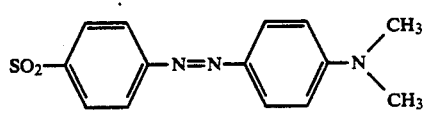

wherein
Q represents alkyl, aryl or aralkyl groups of amino acids of $P_1$ and $P_2$ wherein
$P_1$ and $P_2$ are non-acylated chains of a gelatin hydrolyzate which are not modified chemically by addition or nucleophilic substitution, and
T represents NH;
(6) a colored protein derivative having formula (I) given above wherein unit A is approximately 12 weight percent of said protein derivative, M represents $(CH_3CH_2)_3NH$ and -XY has the formula

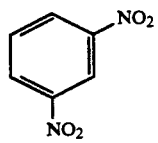

wherein
Q represents alkyl, aryl or aralkyl groups of amino acids of $P_1$ and $P_2$ wherein
$P_1$ and $P_2$ are non-acylated chains of a gelatin hydrolyzate which are not modified chemically by addition or nucleophilic substitution, and
T represents NH;
(7) a colored protein derivative having formula (I) given above wherein unit A is approximately 5 percent by weight of said protein derivative, M represents hydrogen and -XY has the formula

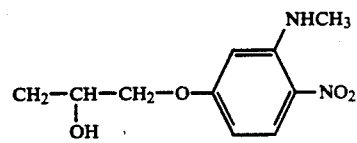

wherein

Q represents alkyl, aryl or aralkyl groups of amino acids of $P_1$ and $P_2$ wherein $P_1$ and $P_2$ are non-acylated chains of a gelatin hydrolyzate which are not modified chemically by addition or nucleophilic substitution, and T represents NH or O; and (8) a colored protein derivative having formula (I) given above wherein unit A is approximately 14 weight percent of said protein derivative, M represents hydrogen and -XY has the formula

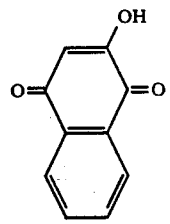

wherein

Q represents alkyl, aryl or aralkyl groups of amino acids of $P_1$ and $P_2$ wherein $P_1$ and $P_2$ are non-acylated chains of a gelatin hydrolyzate which are not modified chemically by addition or nucleophilic substitution, and T represents NH; and mixtures thereof.

* * * * *